United States Patent [19]

Seibert et al.

[11] Patent Number: 4,774,017
[45] Date of Patent: Sep. 27, 1988

[54] THICKENING AGENT FOR DETERGENT CONTAINING PREPARATIONS

[75] Inventors: Karl Seibert, Duren-Niederau; Klaus Neumann, Kreuzau-Obermaubach; Ernst Spiess, Erfstadt-Gymnich, all of Fed. Rep. of Germany; Hendrick G. Bruil, Irenelaan, Netherlands

[73] Assignee: Akzona Incorporated, Asheville, N.C.

[21] Appl. No.: 854,073

[22] Filed: Apr. 17, 1986

Related U.S. Application Data

[63] Continuation of Ser. No. 710,173, Mar. 11, 1985, abandoned, which is a continuation of Ser. No. 470,803, Feb. 28, 1983, abandoned.

[30] Foreign Application Priority Data

Mar. 3, 1982 [DE] Fed. Rep. of Germany ....... 3207613
Jan. 26, 1983 [DE] Fed. Rep. of Germany ....... 3302465

[51] Int. Cl.$^4$ .................. C11D 3/20; C07C 43/11; C07C 43/18; C07C 43/20
[52] U.S. Cl. .................. 252/174.12; 252/170; 252/174.22; 252/DIG. 1; 252/DIG. 2; 568/608; 568/625
[58] Field of Search ........ 252/174.12, 174.22, 252/170, DIG. 1, DIG. 2; 568/608, 625

[56] References Cited

U.S. PATENT DOCUMENTS

| | | | |
|---|---|---|---|
| 3,036,130 | 5/1962 | Jackson et al. | 568/625 X |
| 4,207,421 | 6/1980 | Scardera et al. | 252/174.21 X |
| 4,280,919 | 7/1981 | Stoeckigt et al. | 568/625 X |
| 4,288,639 | 9/1981 | Camp | 568/625 |
| 4,302,349 | 11/1981 | Kosswig et al. | 252/174.21 |
| 4,304,902 | 12/1981 | Landoll | 568/625 X |
| 4,354,956 | 10/1982 | Camp | 252/316 |
| 4,521,326 | 6/1985 | Seibert et al. | 252/174.21 |

FOREIGN PATENT DOCUMENTS

P24327579 1/1976 Fed. Rep. of Germany .

*Primary Examiner*—Paul R. Michl
*Assistant Examiner*—Mukund J. Shah
*Attorney, Agent, or Firm*—Parkhurst & Oliff

[57] ABSTRACT

A thickening agent comprising polyether derivatives of the general formula:

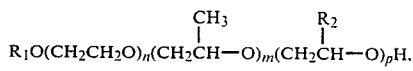

$$R_1O(CH_2CH_2O)_n(CH_2CH-O)_m(CH_2CH-O)_pH,$$
with $CH_3$ and $R_2$ substituents wherein $R_1$ is a substituted or unsubstituted hydrocarbon radical or an alkylphenol radical having 10 or more carbon atoms, n is 10 to 100, m is 0 to 25, and p is 1 to 3, and wherein $R_2$ is an alkyl radical having 8 to 30 carbon atoms. These polyether derivatives are prepared by the gradual addition of a long-chain 1,2-epoxy having a chain length of 10 to 32 carbon atoms at temperatures from 100° to 200° C., to either (1) a polyethylene glycol monoether having an average molecular weight of 800 to 5000, the monoether group thereof being a substituted or unsubstituted hydrocarbon radical having at least 10 carbon atoms; or to (2) a polyethylene glycol-polypropylene glycol monoether with an average molecular weight of 850 to 6300, and having repeating ethylene oxide and propylene oxide units each forming a polyethylene glycol and polypropylene glycol block, respectively, the polypropylene glycol block having an average molecular weight of no more than 1300, and the monoether group forming the end of the polyethylene glycol block and being a substituted or unsubstituted hydrocarbon radical having at least 10 carbon atoms. This thickening agent is prepared using 0.1 to 1.0% by weight of an alkali hydroxide; referring to the total quantity of the long-chain epoxy and the monoether.

7 Claims, 1 Drawing Sheet

THICKENING AGENT FOR DETERGENT CONTAINING PREPARATIONS

This is a continuation of application Ser. No. 710,173, filed Mar. 11, 1985, now abandoned, which in turn is a continuation of application Ser. No. 470,803, filed Feb. 28, 1983, now abandoned.

BACKGROUND OF THE INVENTION

The invention refers to thickening agents based upon polyether derivatives. Thickening agents are used for the thickening of natural and synthetic oils, aqueous electrolyte solutions, and aqueous solutions of organic substances. Their use facilitates the handling of liquids used as household chemicals. Thickening agents are also customarily used in electrolyte solutions, which are required in batteries. Heretofore, waxes, carboxyalkyl celluloses, starch, xanthan gum, or high-molecular esters have been used as thickening agents.

It is customary to use thickening agents for cosmetic, detergent-containing preparations so as to stabilize the disperse systems and for better handling during use. In the case of ether sulfates, it is customary to thicken the preparations with inorganic electrolytes, preferably with common salt. In the case of other detergents, use is, for example, made of distearyl polyglycolester, cellulose derivatives, or natural and synthetic soluble polymers. The preparations obtained in this manner exhibit a behavior that is structurally viscous and/or thixotropic.

According to DIN 53900, detergents are chemical compounds which, when dissolved or dispersed in a liquid, are preferentially adsorbed on an interface. A number of physicochemical or chemical characteristics of practical significance result. The expression "interface-active compound" is herein used synonymously with "detergent". Further, "detergent-containing preparations" are defined herein as mixtures containing detergents as essential constituents.

The object of the present invention was to find a thickening agent having the viscosity behavior of a Newtonian liquid and, in addition, having hydrolysis-resistance under customary conditions of use.

SUMMARY OF THE INVENTION

The present invention is a thickening agent comprising a polyether derivative prepared by the gradual addition of a long-chain 1,2-epoxy having a chain length of 10 to 32 carbon atoms, at temperatures from 100° to 200° C., to either (1) a polyethylene glycol monoether having an average molecular weight of 800 to 5000, the monoether group being a substituted or unsubstituted hydrocarbon radical having at least 10 carbon atoms; or to (2) a polyethylene glycol-polypropylene glycol monoether with an average molecular weight of 850 to 6300, and having repeating ethylene oxide and propylene oxide units each forming a polyethylene glycol and polypropylene glycol block, respectively, the polypropylene glycol block having an average molecular weight of no more than 1300, the monoether group forming the end of the polyethylene glycol block and being a substituted or unsubstituted hydrocarbon radical having at least 10 carbon atoms, and wherein the agent is prepared using 0.1 to 1% by weight of an alkali hydroxide, the weight being based upon the total weight of the long-chain epoxy and the monoether. The polyether derivative corresponds to the general formula:

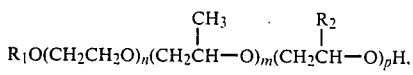

wherein $R_1$ is a substituted or unsubstituted hydrocarbon or alkyl phenol radical having 10 or more carbon atoms, n is 10 to 100, m is 0 to 25 and p is 1 to 3, and wherein $R_2$ is an alkyl radical having 8 to 30 carbon atoms. The values of n, m, and p, wherever they appear in the present specification and claims, are to be understood as representing average values.

Preferably, the ether group ($R_1$) is an aliphatic hydrocarbon radical with 10 to 22 carbon atoms. Yet another preferred embodiment is the present polyether derivatives wherein the ether group ($R_1$) is a straight-chained hydrocarbon radical, and good thickening agents are also obtained when the ether group is an alkylphenol radical having an alkyl chain length of 7 to 15 carbon atoms. The preferred chain length of the long-chain epoxy is from 12 to 20 carbon atoms, that is, where $R_2$ contains from 10 to 18 carbon atoms.

DESCRIPTION OF THE PREFERRED EMBODIMENTS

Figure 1:
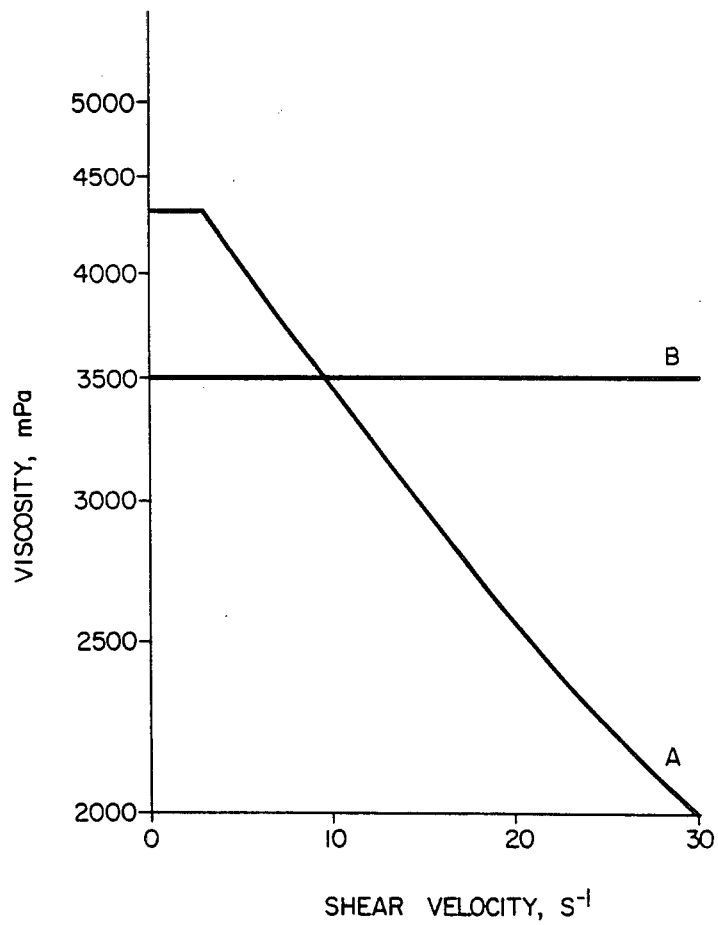

The manufacture is carried out in a manner analogous to the reactions of alcohols with 1,2-epoxies described in Houben-Weyl, *Methoden der organischen Chemie* (Methods of Organic Chemistry), vol. 14.2, pp. 436–450. Pursuant to the invention, the thickening agent is used for anhydrous, liquid systems, such as polyalkylene glycols; special fatty acid esters like trimethylol propaneoleate or diisodecyl adipate; organic salts, for example, diethanolamine salts; or vegetable oils, such as soybean oil or castor oil; for detergent-free aqueous solutions, as for example acid solutions, electrolyte solutions or alcohol solutions; or for detergent-containing preparations, whereby the content of polyether derivative in the detergent-containing preparation amounts to 0.5 to 10% by weight, referred to the weight of the preparation. The detergent-containing preparation may be used as a household cleaning agent, cosmetic emulsion or cosmetic gel, hairdressing preparation, foam bath, or the like. Detergent-containing preparations making use of the polyether derivative pursuant to the invention may also be used in liquids for hydraulic purposes, in treatment liquids for the cutting or non-cutting processing of materials, or the like.

Preferably, the concentration of detergents in detergent-containing preparations incorporating the present polyether derivative is 1 to 40% by weight. At this concentration, the detergents partially solubilize the thickening agent. This effect is particularly pertinent to the detergent-containing preparations such as hydraulic fluids or liquids for the cutting or non-cutting type processing of materials. In addition to the aforementioned applications, detergent-containing preparations with thickening agents are also employed in the foodstuff industry, for example, as a sugar anti-crystallant or for the fixing of flavors. Such preparations are also useful in paper making and the textile industry.

For an improvement of their handling, detergent-free or detergent-containing household chemicals may be thickened with the thickening agents pursuant to the invention to reach higher viscosities. These include acids for cleaning purposes in hospital areas, alcohol solutions for cleaning and care purposes, and stripping agents for coats of paint. Naturally, the thickening agents pursuant to the invention can also be used for detergent-free preparations intended for the food industry, as well as for electrolyte solutions for batteries, and also for vegetable oils such as castor oil and soybean oil.

The following examples, while not intended to be limiting, demonstrate several preferred embodiments of the invention.

EXAMPLE 1

Thickening agents pursuant to the invention are prepared by mixing at 80° C. 0.2 mole of a fatty alcohol ethoxylate melt with 0.5% of 90% potassium hydroxide powder in a three-necked flask equipped with stirrer and descending condenser. The percentage of the alkali hydroxide added herein is based upon the total weight of all ingredients used to manufacture the thickening agent, i.e., the fatty alcohol ethoxylate and the epoxyalkane. Nitrogen is passed through the flask, while the temperature is held at 80° C. for 30 minutes. The contents are then heated to 140° C. under a water-jet vacuum (12 to 14 Torr), maintaining the vacuum for 30 minutes. After releasing the vacuum by adding nitrogen, 0.2 mole of epoxyalkane is added drop-by-drop over one hour. The epoxy reaction is completed after an additional two hour reaction time. The mix is cooled to 80° C. and the pH is adjusted to 6.5–7 with glacial acetic acid. The products prepared according to this procedure and their characteristics are listed in the following table:

TABLE 1

| Product | $R_1$ | n | $R_2$ | Average Molecular Weight | Flow Range | Appearance |
|---|---|---|---|---|---|---|
| A | oleyl | 40 | decyl | 2450 | 44–45° C. | yellowish wax |
| B | nonylphenol | 50 | decyl | 2150 | 43–45° C. | brownish wax |
| C | tallow radical | 60 | dodecyl | 2800 | 48° C. | clear wax |
| D | tallow radical | 80 | decyl | 3400 | 49–51° C. | yellowish wax |

EXAMPLE 2

Using the thickening agents prepared in Example 1, detergent-containing preparations were formulated with the various detergents whose chemical compositions are shown in Table 3. The viscosity of these preparations was determined at 20° C. with a Couette rotation viscometer, model Haake CV 100.

Detergent-containing preparations similar to those of the present invention but using sodium chloride and polyethylene glycol-6000-distearate instead of the present polyether derivatives were prepared for comparison purposes and are listed at Examples 2(j), (k), (s), and (t). Examples 2(r) and (t) show the difference in storage stability between detergent-containing preparations containing the thickening agent pursuant to the invention and that of detergent-containing preparations containing the known stabilizer, polyethylene glycol-6000-distearate. Upon measuring the viscosities of the two detergent-containing preparations after 25 days of storage at 50° C., the viscosity of the product pursuant to the invention remained practically constant, whereas the viscosity of the comparison product dropped to about 1/20th of its original viscosity. The results of the viscosity measurements for Examples 2(a) to (t) have been compiled in Table 2, which also shows the composition of the detergent-containing preparation in question.

FIG. 1 demonstrates the dependence of the viscosity upon the shear velocity for Example 2(k) (curve A) and 2(l) (curve B). From the curves, it is apparent that the use of the present thickening agent imparts Newtonian (shear-independent) viscosity characteristics to detergent-containing preparations. In contrast, when common salt is used in corresponding detergent-containing preparations, the preparations exhibit a structurally viscous (shear-dependent) behavior. Thickening agents are intended to raise the viscosity of detergent-containing preparations and maintain that viscosity regardless of external factors, and it is thus undesirable when the viscosity declines at higher shear velocities.

TABLE 2

| Example | Detergent (Table 3) | Detergent Concentration, % | Thickening Agent (Table 1) | Ratio, Thickening Agent/Detergent | Viscosity (20° C.) mPa s | at a shear rate, $s^{-1}$ | Rheolog. Behavior |
|---|---|---|---|---|---|---|---|
| a | R | 7 | C | 1:1.4 | 1,300 | 50 | Newtonian |
| b | R | 21 | C | 1:4.2 | 6,500 | 20 | " |
| c | R | 14 | C | 1:3.5 | 620 | 150 | " |
| d | R | 14 | C | 1:1.75 | 44,000 | 3 | " |
| e | R | 2 | C | 2.5:1 | 30 | 300 | " |
| f | R | 14 | D | 1:3.5 | 450 | 150 | " |
| g | S | 18 | B | 1:2.6 | 160 | 90 | " |
| h | T | 15 | A | 1:2.5 | 990 | 90 | " |
| i | R | 14 | — | — | 3 | 300 | " |
| j | R | 14 | NaCl | 1:3.5 | 9 | 300 | " |
| k | U | 14 | NaCl | 1:4.7 | 2,000 | 30 | struc. viscous |
| l | U | 14 | C | 1:2.8 | 3,500 | 30 | Newtonian |
| m | V | 14 | C | 1:2.8 | 700 | 150 | " |
| n | W | 14 | C | 1:2.8 | 3,500 | 30 | " |
| o | X | 14 | C | 1:2.8 | 250 | 150 | " |
| p | Y | 14 | C | 1:2.8 | 250 | 150 | " |
| q | R | 14 | C | 1:2.3 | 14,400 | 12 | " |
| r | R | 14 | C | 1:2.3 | 14,300 | 12 | "** |
| s | R | 14 | Z | 1:2.3 | 3,290 | 60 | " |
| t | R | 14 | Z PLG 6000 di-stearate | 1:2.3 | 170 | 60 | "** |

**After 25 days of storage at 50° C.

TABLE 3

| Type | | |
|---|---|---|
| Detergent | | |
| R | anionic | alpha-olefin sulfonate (sodium salt), based upon a $C_{14}$-$C_{16}$ alphaolefin |
| S | anionic | sulfosuccinic monoester (disodium salt) based upon an ethoxylated fatty acid alkylol |
| T | nonionogenic/cationic | dimethylcocosamine oxide |
| U | anionic | alkylethersulfate (sodium salt) based upon a $C_{12}$-$C_{15}$ ethoxylated fatty alcohol with 2.5 moles ethylene oxide |
| V | anionic | alkylsulfate (triethanolamine salt) based upon a $C_{12}$-$C_{14}$ fatty alcohol |
| W | amphoteric betaine type | fatty acid amidopropyl-dimethylaminoacetic acid |
| X | nonionogenic | sorbitan monolaurate, ethoxylated, with about 20 moles ethylene oxide |
| Y | cationic | alkyldimethyl benzyl ammoniumchloride based upon $C_{12}$-$C_{14}$ alkyl group |
| Thickening agent | | |
| Z | | polyethylene glycol-6000-distearate |

EXAMPLE 3

The thickening agent designated Product C in Example 1 (Table 1), which had first been melted at 75° C., was added with stirring to aqueous solutions of hydrochloric acid, sulfuric acid, orthophosphoric acid, citric acid, common salt, calcium chloride, urea, ethylene glycol, glycerin and D(-)sorbitol, which had been heated to 75° C. After cooling to room temperature, the solutions are clear as water, stable, and viscous.

Viscous, aqueous solutions of ethanol and isopropanol were prepared as follows. At 75° C., the melted thickening agent referred to as Product C in Example 1 (Table 1), was added with stirring to water at 75° C. After cooling to about 30° C., ethanol or isopropanol was added with stirring. After cooling to room temperature, the solutions are clear as water, stable, and viscous.

The viscosity of the aqueous, viscous systems was measured at 25° C. with a KPG-Ubbelohde viscometer with suspended ball level, DIN 51562. The kinematic viscosity is expressed in cST. The compositions of the mixtures and the results of the viscosity measurements are compiled in Table 4.

TABLE 4

Thickening of aqueous solutions of electrolytes and alcohols with Thickening Agent C (Table 1).

| Examples | | Solution to be thickened | Conc. of solution % | Concentration of thickened subst. % | Viscosity cST, 25° C. |
|---|---|---|---|---|---|
| | | water | — | 10 | 250 |
| I | | hydrochloric acid | 10 | — | 1.02 |
| I | a. | hydrochloric acid | 10 | 10 | 215 |
| II | | sulfuric acid | 10 | — | 1.08 |
| II | a. | sulfuric acid | 10 | 10 | 823 |
| III | | orthophosphoric acid | 10 | — | 1.17 |
| III | a. | orthophosphoric acid | 10 | 10 | 810 |
| IV | | citric acid | 9 | — | 1.08 |
| IV | a. | citric acid | 9 | 9 | 90 |
| IV | b. | citric acid | 18 | — | 1.31 |
| IV | c. | citric acid | 18 | 9 | 115 |
| IV | d. | citric acid | 27 | — | 1.63 |
| IV | e. | citric acid | 27 | 9 | 170 |
| V | | sodium chloride | 10 | — | 1.01 |
| V | a. | sodium chloride | 10 | 10 | 425 |
| VI | | calcium chloride | 10 | — | 1.11 |
| VI | a. | calcium chloride | 10 | 10 | 400 |
| VII | | urea | 10 | — | 0.97 |
| VII | a. | urea | 10 | 10 | 823 |
| VIII | | ethanol | 9 | — | 1.27 |
| VIII | a. | ethanol | 9 | 9 | 72 |
| VIII | b. | ethanol | 18 | — | 1.72 |
| VIII | c. | ethanol | 18 | 9 | 50 |
| IX | | propanol-2 | 9 | — | 1.38 |
| IX | a. | propanol-2 | 9 | 9 | 108 |
| IX | b. | propanol-2 | 18 | — | 2.01 |
| IX | c. | propanol-2 | 18 | 9 | 51 |
| X | | ethylene glycol | 9 | — | 1.11 |
| X | a. | ethylene glycol | 9 | 9 | 66 |
| X | b. | ethylene glycol | 18 | — | 1.34 |
| X | c. | ethylene glycol | 18 | 9 | 72 |
| XI | | glycerin | 9 | — | 1.12 |
| XI | a. | glycerin | 9 | 9 | 57 |
| XI | b. | glycerin | 18 | — | 1.45 |
| XI | c. | glycerin | 18 | 9 | 75 |
| XII | | D(—)sorbitol | 9 | — | 1.14 |
| XII | a. | D(—)sorbitol | 9 | 9 | 81 |
| XII | b. | D(—)sorbitol | 18 | — | 1.48 |
| XII | c. | D(—)sorbitol | 18 | 9 | 134 |

EXAMPLE 4

The liquids numbered W1 to W8 in Table 5 were thickened with thickening agent C in Example 1 (Table 1) by finely dispersing the thickening agent with stirring at temperatures between 70° and 90° C. After cooling to room temperature, the resulting dispersions were turbid, but stable and viscous. The viscosities of these non-aqueous, stable, viscous dispersions, as well as those of the corresponding liquids without the addition of thickening agent, were measured at 25° C. with a Brookfield synchrolectric viscometer, model LVT. The dynamic viscosity is expressed in cP. The results are likewise compiled in Table 5.

TABLE 5

| Experiment | Liquids | | Conc. of thickening agent (%) (C of Table 1) | Viscosity cP, 25° C. | (Brookfield) rpm | spindle |
|---|---|---|---|---|---|---|
| I | W1 | polyethylene glycol 400 | — | 95 | 12 | 4 |
| Ia | | | 5 | 10,000 | 12 | 4 |
| II | W2 | polyethylene glycol 400-monoester of an isomeric oleic acid | — | 100 | 12 | 4 |
| IIa | | | 5 | 3,500 | 12 | 4 |
| III | W3 | diethanolamine salt of an isomeric oleic acid | — | 1,040 | 12 | 4 |
| IIIa | | | 5 | 20,000 | 12 | 4 |
| IV | W4 | trimethylol propane | — | 190 | 12 | 4 |

TABLE 5-continued

| Experiment | | Liquids | Conc. of thickening agent (%) (C of Table 1) | Viscosity cP, 25° C. | (Brookfield) rpm | spindle |
|---|---|---|---|---|---|---|
| IVa | | oleate | 5 | 12,500 | 12 | 4 |
| V | W5 | trimethylol propane ester | — | 30 | 12 | 3 |
| Va | | $C_8$-$C_{10}$ fatty acids | 5 | 1,900 | 12 | 3 |
| VI | W6 | diisodecyl adipate | — | 16 | 12 | 3 |
| VIa | | | 5 | 1,700 | 12 | 3 |
| VII | W7 | soybean oil type SEH | — | 50 | 12 | 4 |
| VIIa | | | 5 | 1,500 | 12 | 4 |
| VIII | W8 | castor oil, DIN | — | 625 | 12 | 4 |
| VIIIa | | 55939, DRO brand | 5 | 18,500 | 12 | 4 |

What is claimed is:

1. A thickening agent comprising a polyether compound of the formula

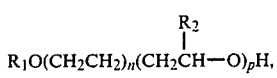

wherein:
R$_1$ is a substituted or unsubstituted aliphatic hydrocarbon radical having 10 to 22 carbon atoms or alkylphenol radical having an alkyl chain length of 7 to 15 carbon atoms;
R$_2$ is an alkyl radical having 8 to 30 carbon atoms;
n=40 to 80; and
p=1 to 3;
said compound being water soluble and solid at room temperature.

2. A thickening agent according to claim 1, wherein R$_1$ is a tallow radical.

3. A thickening agent according to claim 1, wherein R$_2$ is an alkyl radical having 10 to 18 carbon atoms.

4. A thickening agent according to claim 1, wherein p=1.

5. A thickening agent according to claim 2, wherein p=1.

6. A thickening agent according to claim 3, wherein p=1.

7. A thickening agent according to claim 1, wherein said compound has an average molecular weight in the range of about 2150 to 3400.

* * * * *

UNITED STATES PATENT AND TRADEMARK OFFICE
CERTIFICATE OF CORRECTION

PATENT NO. : 4,774,017

DATED : September 27, 1988

INVENTOR(S) : Karl SEIBERT et al

It is certified that error appears in the above-identified patent and that said Letters Patent is hereby corrected as shown below:

Column 3, after Table 1, insert the following:

--tallow radical = mixture of saturated hydrocarbon radicals with 16 to 18 carbon atoms.--

Signed and Sealed this

Twenty-eighth Day of February, 1989

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,774,017
DATED : September 27, 1988
INVENTOR(S) : K. SEIBERT et al It is certified that error appears in the above-identified patent and that said Letters Patent is hereby corrected as shown below:

Claim 1, line 3, change the formula to read:

$$-- R_1O(CH_2CH_2O)_n (CH_2\overset{\overset{R_2}{|}}{C}H-O)_pH, --$$

Signed and Sealed this

Twentieth Day of June, 1989

Attest:

Attesting Officer

DONALD J. QUIGG

Commissioner of Patents and Trademarks